(12) United States Patent
Blum et al.

(10) Patent No.: US 10,226,600 B2
(45) Date of Patent: Mar. 12, 2019

(54) SYSTEM AND METHOD FOR ENHANCED MANEUVERABILITY

(75) Inventors: Yoram Blum, Givat Shmuel (IL); Eran Shor, Moshav Arugot (IL); Ran Mendelewicz, Herzliya (IL)

(73) Assignee: G.I. VIEW LTD., Ramat Gan (IL)

( * ) Notice: Subject to any disclaimer, the term of this patent is extended or adjusted under 35 U.S.C. 154(b) by 839 days.

(21) Appl. No.: 13/056,350

(22) PCT Filed: Jul. 30, 2009

(86) PCT No.: PCT/IL2009/000748
§ 371 (c)(1),
(2), (4) Date: Mar. 11, 2011

(87) PCT Pub. No.: WO2010/013247
PCT Pub. Date: Feb. 4, 2010

(65) Prior Publication Data
US 2011/0160536 A1 Jun. 30, 2011

Related U.S. Application Data

(60) Provisional application No. 61/137,509, filed on Jul. 30, 2008.

(51) Int. Cl.
*A61B 1/04* (2006.01)
*A61M 25/10* (2013.01)
(Continued)

(52) U.S. Cl.
CPC ... *A61M 25/10181* (2013.11); *A61B 1/00147* (2013.01); *A61B 1/015* (2013.01);
(Continued)

(58) Field of Classification Search
CPC ......... A61M 25/10184; A61B 1/00147; A61B 1/00156
(Continued)

(56) References Cited

U.S. PATENT DOCUMENTS 3,895,637 A 7/1975 Choy
3,924,625 A 12/1975 Peterson
(Continued)

FOREIGN PATENT DOCUMENTS

EP 0 242 428 10/1987
EP 0 659 387 6/1995
(Continued)

OTHER PUBLICATIONS

U.S. Appl. No. 60/571,438, filed May 14, 2004, Gideon Dotan, Yehud.
(Continued)

*Primary Examiner* — Alexandra L Newton
*Assistant Examiner* — Rynae Boler
(74) *Attorney, Agent, or Firm* — Dorsey & Whitney LLP

(57) ABSTRACT

The present invention relates to an imaging apparatus comprising an elongated carrier adapted to be inserted through a proximal opening of a gastrointestinal (GI) tract lumen; a piston head, coupled to a distal portion of the carrier, and configured to: be inflated so as to form and maintain a pressure seal with a wall of the GI tract lumen, and be advanced distally through the GI tract in response to pressure from a fluid pressure source; a distal balloon coupled to the carrier distal to the piston head and configured and operable to be inflated so as to dilate the lumen thereby creating a working space; and a control unit, configured and operable to control simultaneously a pressure level within the piston head and a pressure level within the distal balloon. The control comprises maintaining a constant level of pressure within the piston head thereby maintaining said pressure seal and cyclically modulating the level of pressure within the distal balloon facilitating the distal advancement of the piston head within the GI tract lumen.

5 Claims, 3 Drawing Sheets

(51) Int. Cl.
*A61B 1/00* (2006.01)
*A61B 1/015* (2006.01)
*A61M 25/01* (2006.01)
*A61M 29/02* (2006.01)

(52) U.S. Cl.
CPC ........ *A61M 25/0122* (2013.01); *A61M 29/02* (2013.01); *A61M 25/1011* (2013.01); *A61M 25/10184* (2013.11); *A61M 2025/1052* (2013.01); *A61M 2210/1064* (2013.01)

(58) Field of Classification Search
USPC ........ 600/116, 115; 604/97.01, 97.03, 98.01, 604/101.01, 101.05
See application file for complete search history.

(56) References Cited

U.S. PATENT DOCUMENTS

| | | |
|---|---|---|
| 4,040,413 A | 8/1977 | Ohshiro |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,224,929 A | 9/1980 | Furihata |
| 4,278,077 A | 7/1981 | Mizumoto |
| 4,327,722 A | 5/1982 | Groshong et al. |
| 4,403,985 A | 9/1983 | Boretos |
| 4,530,698 A | 7/1985 | Goldstein et al. |
| 4,561,427 A | 12/1985 | Takada |
| 4,566,763 A | 1/1986 | Greguss |
| 4,596,381 A | 6/1986 | Hamrick |
| 4,690,131 A | 9/1987 | Lyddy, Jr. et al. |
| 4,737,142 A | 4/1988 | Heckele |
| 4,838,859 A | 6/1989 | Strassmann |
| 4,971,034 A | 11/1990 | Doi et al. |
| 4,976,524 A | 12/1990 | Chiba |
| 4,995,396 A | 2/1991 | Inaba et al. |
| 5,152,277 A * | 10/1992 | Honda et al. .................. 600/116 |
| 5,259,364 A | 11/1993 | Bob et al. |
| 5,337,732 A | 8/1994 | Grundfest et al. |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A | 3/1995 | Ortiz et al. |
| 5,471,988 A | 12/1995 | Fujio et al. |
| 5,473,474 A | 12/1995 | Powell |
| 5,476,505 A | 12/1995 | Limon |
| 5,509,371 A | 4/1996 | Phillips |
| 5,571,114 A | 11/1996 | Devanaboyina |
| 5,575,754 A | 11/1996 | Konomura |
| 5,586,968 A | 12/1996 | Grundl et al. |
| 5,604,531 A | 2/1997 | Iddan et al. |
| 5,662,587 A * | 9/1997 | Grundfest .......... A61B 1/00082 600/114 |
| 5,728,068 A | 3/1998 | Leone et al. |
| 5,740,808 A | 4/1998 | Panescu et al. |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,130,783 A | 10/2000 | Yagi et al. |
| 6,157,018 A | 12/2000 | Ishiguro et al. |
| 6,277,065 B1 | 8/2001 | Donofrio |
| 6,296,608 B1 | 10/2001 | Daniels et al. |
| 6,315,713 B1 | 11/2001 | Takada |
| 6,332,865 B1 | 12/2001 | Borody et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,439,032 B1 | 8/2002 | Lehmann |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi |
| 6,517,477 B1 | 2/2003 | Wendlandt |
| 6,527,705 B1 | 3/2003 | Ouchi |
| 6,537,206 B2 | 3/2003 | Takada |
| 6,544,216 B1 | 4/2003 | Sammler et al. |
| 6,587,724 B2 | 7/2003 | Mann |
| 6,597,520 B2 | 7/2003 | Wallerstein et al. |
| 6,599,237 B1 | 7/2003 | Singh |
| 6,609,032 B1 | 8/2003 | Woods et al. |
| 6,611,282 B1 | 8/2003 | Trubko et al. |
| 6,632,227 B2 | 10/2003 | Adams |
| 6,646,818 B2 | 11/2003 | Doi |
| 6,648,814 B2 | 11/2003 | Kim et al. |
| 6,682,479 B1 | 1/2004 | Takahashi et al. |
| 6,695,771 B2 | 2/2004 | Takada |
| 6,702,734 B2 | 3/2004 | Kim et al. |
| 6,702,735 B2 | 3/2004 | Kelly |
| 6,704,148 B2 | 3/2004 | Kumata |
| 6,709,388 B1 | 3/2004 | Mosse et al. |
| 6,743,208 B1 | 6/2004 | Coyle |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler |
| 6,911,005 B2 | 6/2005 | Ouchi et al. |
| 6,932,323 B2 | 8/2005 | James |
| 6,974,441 B2 | 12/2005 | Ravo |
| 7,056,283 B2 | 6/2006 | Baror et al. |
| 2001/0041874 A1 | 11/2001 | Reydel |
| 2002/0012059 A1 | 1/2002 | Wallerstein et al. |
| 2002/0072651 A1 | 6/2002 | Vilos |
| 2002/0107478 A1 | 8/2002 | Wendlandt |
| 2002/0109772 A1 | 8/2002 | Kuriyama et al. |
| 2002/0109773 A1 | 8/2002 | Kuriyama et al. |
| 2003/0000526 A1 | 1/2003 | Gobel |
| 2003/0074015 A1 | 4/2003 | Nakao |
| 2003/0083547 A1 | 5/2003 | Hamilton et al. |
| 2003/0105386 A1 | 6/2003 | Voloshin et al. |
| 2003/0153866 A1 | 8/2003 | Long et al. |
| 2003/0168068 A1 | 9/2003 | Poole et al. |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0111019 A1 | 6/2004 | Long |
| 2004/0111020 A1 | 6/2004 | Long |
| 2004/0143161 A1 | 7/2004 | Baror et al. |
| 2004/0147806 A1 * | 7/2004 | Adler ............................ 600/109 |
| 2004/0199087 A1 | 10/2004 | Swain et al. |
| 2004/0199088 A1 | 10/2004 | Bakos et al. |
| 2004/0199196 A1 * | 10/2004 | Ravo ............................ 606/194 |
| 2004/0204702 A1 | 10/2004 | Ziegler et al. |
| 2004/0249247 A1 | 12/2004 | Iddan |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0085841 A1 | 4/2005 | Eversull et al. |
| 2005/0095200 A1 | 5/2005 | Schwarzberg |
| 2005/0107664 A1 | 5/2005 | Kalloo et al. |
| 2005/0154355 A1 * | 7/2005 | Gross et al. .................. 604/232 |
| 2005/0165272 A1 | 7/2005 | Okada et al. |
| 2005/0197531 A1 | 9/2005 | Cabiri et al. |

(56) References Cited

U.S. PATENT DOCUMENTS

| | | | |
|---|---|---|---|
| 2005/0222496 A1* | 10/2005 | Sekiguchi | A61B 1/00082 600/115 |
| 2006/0111611 A1 | 5/2006 | Eizenfeld et al. | |
| 2006/0164733 A1 | 7/2006 | Gal et al. | |
| 2006/0238879 A1 | 10/2006 | Togino | |
| 2007/0010785 A1* | 1/2007 | Sekiguchi | A61B 1/00082 604/95.03 |

FOREIGN PATENT DOCUMENTS

| | | |
|---|---|---|
| EP | 1 586 275 | 10/2005 |
| FR | 1465723 | 3/1967 |
| JP | 5-43114 | 6/1993 |
| JP | 10-216076 | 8/1998 |
| JP | 10 309259 | 11/1998 |
| JP | 2002 31766 | 1/2002 |
| JP | 2005-278846 | 10/2005 |
| JP | 2005-312903 | 11/2005 |
| JP | 2006 26344 | 2/2006 |
| JP | 2007-517576 | 7/2007 |
| JP | 2007-268147 | 10/2007 |
| WO | WO 99/40957 | 8/1999 |
| WO | WO 00/44275 | 8/2000 |
| WO | WO 01/68540 | 9/2001 |
| WO | WO 02/059676 | 8/2002 |
| WO | WO 02/075348 | 9/2002 |
| WO | WO02068035 A1 | 9/2002 |
| WO | WO 03/026272 | 3/2003 |
| WO | WO 03/045487 | 6/2003 |
| WO | WO 03/046830 | 6/2003 |
| WO | WO 03/053225 | 7/2003 |
| WO | WO 2004/008185 | 1/2004 |
| WO | WO 2004/010858 | 2/2004 |
| WO | WO 2004/016299 | 2/2004 |
| WO | WO04028354 A1 | 4/2004 |
| WO | WO 2004/049905 | 6/2004 |
| WO | WO 2004/069057 | 8/2004 |
| WO | WO 2005/065044 | 7/2005 |
| WO | WO 2006/025045 | 3/2006 |

OTHER PUBLICATIONS

U.S. Appl. No. 60/607,986, filed Sep. 8, 2004, Oz Cabiri, Macabim.
U.S. Appl. No. 60/490,038, filed Jul. 24, 2003, Benjamin B. James.

* cited by examiner

SYSTEM AND METHOD FOR ENHANCED MANEUVERABILITY

CROSS-REFERENCE TO RELATED APPLICATIONS

This application is a U.S. National Stage of International Application No. PCT/IL2009/000748 filed on Jul. 30, 2009, which claims priority to U.S. Provisional Application Ser. No. 61/137,509 filed on Jul. 30, 2008.

FIELD OF THE INVENTION

The present invention relates generally to a pressure-propelled system, suitable for imaging body lumens, such as the gastrointestinal (GI) tract.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like.

Tubular organs in the body may have a convoluted cavity configuration. The gastrointestinal tract, for example, starts from the oral cavity and proceeds through the esophagus, stomach, duodenum and small intestine, which is a long tube that folds many times to fit inside the abdomen. The small intestine is connected to the large intestine, which begins with the cecum, a small saclike evagination, then continues with the ascending colon, transverse colon, descending colon and the sigmoid (S-shaped) colon to the rectum. These body lumens may suffer from pathologies, which can affect the anatomy or configuration of the lumen. For example, strictures, narrowing or closure of a normally configured lumen can be caused by calcification or by the presence of scar tissue or a tumor.

Traditional colonoscopic examination utilizes a thin, tubular fiber optic probe inserted into the large intestine (colon) via the rectum. A conventional imaging endoscope used for such procedures comprises a flexible tube with a fiber optic light guide that directs illuminating light from an external light source to the distal tip of the endoscope where it illuminates the region (i.e., tissue, occlusive objects) to be examined.

Even the most penetrating colonoscopic inspections are limited to the colon and the terminal portion of the small intestine (ileum), due primarily to the tortuosity and fragility of the large intestine and ileum. Both endoscopic and colonoscopic inspections run a small but significant risk of physical damage to the patient, such as perforation of the duodenum or ileum, especially where disease has progressed to an advanced stage and the surrounding tissue has weakened or degenerated.

PCT Publication WO 05/065044 to Cabiri et al., which is incorporated herein by reference, describes apparatus for use with a biologically-compatible-fluid pressure source, the apparatus including an elongate carrier, adapted to be inserted through a proximal opening of a body lumen, and a piston head coupled to a distal portion of the carrier. The piston head is adapted to form a pressure seal with a wall of the lumen after the carrier has been inserted into the lumen, and to be advanced distally through the body lumen in response to pressure from the fluid pressure source. The apparatus is configured to facilitate distal advancement of the piston head by facilitating passage of fluid out of the lumen from a site within the lumen distal to the piston head. The apparatus additionally includes an optical system, coupled to the carrier in a vicinity of the distal portion, the optical system having distal and proximal ends.

In some embodiments of the PCT application, the apparatus is described as including an auxiliary piston head, coupled to the carrier at a position proximal to the distal piston head. The auxiliary piston head is described as being adapted to be inflated so as to attain and maintain direct contact with the wall of the colon. At least one time while the carrier is within the body lumen, the distal piston head is described as being adapted to be in a state of being already deflated at least in part simultaneously with the auxiliary piston head being already inflated and being advanced distally through the colon in response to pressure from the fluid pressure source. At least one other time while the carrier is within the body lumen, the auxiliary piston head is described as being adapted to be in a state of being already deflated at least in part simultaneously with the distal piston head being already inflated and being advanced distally through the colon in response to pressure from the fluid pressure source.

For example, the PCT application describes that the system may eventually reach an obstacle or tight turn. In such a case, the proximal piston head is described as being inflated and the distal piston head as being deflated. In this configuration, the pressurized fluid is described as creating greater fluid pressure acting on the proximal side of the proximal piston head than on the distal side of the proximal piston head. This pressure difference is described as propelling the proximal piston head together with the carrier distally. This distal movement brings the distal deflated piston head past the obstacle.

The system is described as continuing its distal movement in the body lumen until the proximal piston head reaches the obstacle. At this point, the distal piston head is described as being inflated and the proximal piston head as being deflated. The pressurized fluid is described as creating greater fluid pressure acting on the proximal side of the distal piston head than on the distal side of the distal piston head. The pressure difference is described as propelling the system distally in the body lumen, bringing the proximal deflated piston head past the obstacle. The cycle is described as being repeated as often as necessary.

GENERAL DESCRIPTION

There is a need for an improved imaging medical device being advanced distally through the GI tract and which is especially used as an imaging apparatus navigating into the lower gastrointestinal tract with enhanced maneuverability. Such need is associated with the following. The lower GI tract is made up of the rectum and the large intestine or colon. The colon, extends upwards from the lower right quadrant, traverses the width of the body just below the diaphragm, extends downwards along the left side of the abdomen and then loops in a retrograde manner before linking up with the rectum and the anus. The large intestine is difficult to cannulate with a flexible endoscope due to the flexible nature of the endoscope shaft and the floppy nature of the colon. In some people, the sigmoid colon can be very long and is unfixed, except by its mesentery, and so can be extremely difficult to cannulate due to its predisposition to form loops when an endoscope is pushed through it. Some anatomical landmarks, such as the rectosigmoidal junction, the splenic flexure and the hepatic flexure, are difficult to pass through simply because of their tortuous nature. Problems traversing these areas are exacerbated by looping of the endoscope in the sigmoid colon.

Endoscopy is thus a difficult technique that can only be mastered after performing many hundreds of examinations. The ability to speedily cannulate the bowel and traverse the entire colon all the way to the caecum is a skill that is only enjoyed by a minority of endoscopists. Published research on the subject of difficulty encountered in endoscopy shows that the procedure fails in up to 15 percent of cases where failure is defined as inability to reach or visualise the caecum. Up to 35 percent of cases are considered to be difficult as defined by extended duration of the procedure and experience of pain by the patient. Other research shows that up to 29 percent of cases are considered to be technically difficult.

An endoscope is typically 100-150 centimeters long and may be inserted into either end of the digestive system. Generally, the devices have specific design features adapted to the bodily opening through which the endoscope is inserted. The endoscope is pushed from the bottom and guided through tortuous passages using external manipulation.

The invention provides a novel imaging apparatus, which is generally an imaging apparatus movable through a lumen in a body.

In some embodiments, an elongate carrier is inserted through a proximal opening of a gastrointestinal tract (GI) tract lumen ("proximal" and "distal" being understood as being with respect to the physician). A piston head, coupled to a distal portion of the carrier, is inflated so as to form and maintain a pressure seal with a wall of the GI tract lumen. The piston head is advanced distally through the GI tract in response to pressure from the fluid pressure source. A distal balloon is coupled to the carrier distal to the piston head. A control unit cycles the pressure level within the distal balloon while maintaining the pressure seal. Typically, the control unit cycles the pressure level when distal movement of the piston head is impeded. In some embodiments, the control unit additionally cycles the pressure level within the distal balloon even when distal movement of the piston head is not impeded.

It should thus be understood that for the purposes of the invention, the term "pressure seal" should be interpreted in its general meaning in which occlusion of at least a portion of a body lumen propels the piston head distally.

Some embodiments of the present invention provide an imaging system which is propelled by fluid pressure through a body lumen, such as the gastrointestinal (GI) tract. Embodiments of the invention are described herein with reference to the GI tract, but it is understood that these embodiments are not limited to use in the GI tract, and may be used for other body lumens as well.

There is therefore provided, in accordance with an embodiment of the present invention, apparatus for use with a biologically-compatible-fluid pressure source, including: an elongate carrier, adapted to be inserted through a proximal opening of a gastrointestinal (GI) tract lumen; a piston head, coupled to a distal portion of the carrier, and configured to: be inflated so as to form and maintain a pressure seal with a wall of the GI tract lumen, and be advanced distally through the GI tract in response to pressure from the fluid pressure source; a distal balloon coupled to the carrier, distal to the piston head and configured and operable to be inflated to dilate the lumen thereby creating a working space; and a control unit, configured and operable to control simultaneously the pressure level within the piston head and a pressure level within the distal balloon, said control comprising maintaining a constant level of pressure within the piston head thereby maintaining the pressure seal between the piston head and the wall of the GI tract lumen and cyclically modulating the level of pressure within the distal balloon facilitating the distal advancement of the piston head within the GI tract lumen.

It should be understood that the stomach and other lumens in the GI tract have highly mobile walls and tend to be easily displaced when acted on by a force. They are also highly muscular and expand and contract in various cycles. At any time, the lumen can be open or closed, but is most often in more of a collapsed state. Therefore, the distal balloon of the present invention is configured and operable to dilate the lumen to thereby create a working space within the lumen to facilitate the advancement of the piston head as well as to facilitate the imaging of the lumen. Dilating the body lumen is accomplished by cyclically modulating the pressure within the distal balloon. The balloon therefore creates and stably maintains an imaging working space within a body lumen. This results in a reduction of friction forces of the entire apparatus advancing along the lumen.

It should also be noted that to advance distally the piston head has to be continuously in contact with the walls of the lumen and therefore a pressurized cycled modulation cannot be applied to the piston head.

In an embodiment, the piston head and the distal balloon are arranged in a spaced art configuration of a distance in the range of about 1 mm to 50 mm, preferably 10 mm.

In an embodiment, the hardness of at least a portion of the carrier coupling between the piston head and the distal balloon is selected to be in the range of about 30 to 60 shore A. The portion of the carrier coupling between the distal balloon and the piston head may be a separate or integral portion of carrier. It should be understood that the flexibility of the carrier is a critical feature of the apparatus to be selected appropriately. On one hand, to be inserted into the GI tract, the apparatus has to be flexible enough, and on the other hand, to be advanced within the GI tract and not to be bent, the carrier has to be rigid enough. Therefore, the hardness of at least a portion of the carrier has to be selected to enable insertion and advancement along the GI tract. The hardness can be variable along the carrier. For example, a spring-like member can be introduced within the carrier to control its hardness.

In an embodiment, the control unit is configured and operable to identify impeded movement of the piston head and to cycle the level of pressure within the distal balloon responsively to the identified impeded movement.

In an embodiment, the control unit is configured to cycle the level of pressure within the distal balloon irrespective of any indication of impeded movement of the piston head.

In an embodiment, the control unit is configured to cycle the level of pressure within the distal balloon substantially whenever the pressure seal between the piston head and the wall of the GI tract lumen is maintained during the distal advancement of the piston head.

In an embodiment, the control unit is configured to receive a user-generated input indicative of impeded movement of the piston head, and to cycle the level of pressure within the distal balloon responsively to the input.

In an embodiment, the piston head is configured to have a diameter in the range of about 25 mm to 100 mm while the piston head is in an inflated state thereof.

In an embodiment, a maximum diameter of the distal balloon is in the range of about 10 mm to 65 mm while the control unit cycles the level of pressure within the distal balloon.

In an embodiment, the control unit is configured to cycle the level of pressure within the distal balloon according to a cycle having a length in the range of about 0.5 seconds to 10 seconds, in particular a length in the range of about 2 seconds to 6 seconds.

In an embodiment, the control unit is configured to cycle the level of pressure within the distal balloon according to a cycle having a length in the range of about 1.5 seconds to 4 seconds.

In an embodiment, the control unit is configured to set a minimum pressure level of the distal balloon during a plurality of cycles to be less than 10 mbar, preferably less than 1 mbar and/or to be substantially zero mbar.

In an embodiment, the control unit is configured to set a maximum pressure level of the distal balloon during a plurality of cycles to be in the range of about 20 to 100 mbar. In an embodiment, the apparatus includes a suction source configured to suck fluid from the distal balloon, the control unit being configured to cycle the level of pressure within the distal balloon by controlling the suction source.

In an embodiment, the control unit is configured to cycle the level of pressure within the distal balloon by passively allowing fluid to vent from the distal balloon.

In an embodiment, the control unit is configured to cycle the level of pressure within the distal balloon to selectively collapse or expand a proximal and/or distal ends of the balloon and thus adjust the dimensions of the working space according to the desired clinical result.

In an embodiment, the apparatus comprises at least a first and second fluid pressure sources; a first passageway in fluid communication with the first pressure source and the piston head for inflating the piston head; and a second passageway in fluid communication with the second pressure source and the distal balloon; such that the control unit control simultaneously and independently the pressure level within the piston head and the pressure level within the distal balloon by driving the first pressure source to maintain the pressure seal between the piston head and the wall of the GI tract lumen and by driving the second pressure source to cyclically modulate the level of pressure within the distal balloon.

In an embodiment, the apparatus comprises an image-capturing device configured and operable to image the GI track mounted on the carrier distally to the distal balloon. The distal balloon is configured and operable to create a space between the GI track and the image-capturing device to facilitate the imaging of the GI track.

It should be understood that it is difficult to image the tissue of interest when the image-capturing device is positioned in contact with the lumen. Therefore, the balloon creates a space between the tissue of interest away from the tip of the imaging apparatus in which the image-capturing device is accommodated.

Moreover, it should be understood that the carrier on which the image-capturing device is mounted is flexible and therefore the image-capturing device is attracted downward due to gravity forces. Therefore, the distal balloon is configured and operable to place the carrier near the center of the GI track, such as the colon, whose diameter is larger than that of the carrier, and maintain a longitudinal carrier orientation. The walls of the colon within the panoramic FOV are then nearly equidistant from the image-capturing device, reducing the required depth of field and simplifying exposure.

In an embodiment, the distal balloon has a diameter smaller than the diameter of the piston head in its inflated state.

In other embodiments, the distal balloon forms a pressure seal with the GI track to enable the distal advancement of the apparatus.

There is further provided, in accordance with an embodiment of the present invention, a method including: forming a pressure seal between a piston head and a wall of a gastrointestinal (GI) tract lumen, the piston head being disposed proximally to a distal balloon; advancing the piston head and the distal balloon distally through the lumen by applying fluid pressure to an external surface of the piston head; and cyclically modulating a level of pressure within the distal balloon, while maintaining the pressure seal between the piston head and the wall of the GI tract lumen to dilate the lumen thereby creating an imaging working space through which advancement of the piston head is facilitated.

In an embodiment, forming the pressure seal between the piston head and the wall of the GI tract lumen comprises forming the pressure seal between the piston head and the wall of the GI tract lumen, a distal surface of the piston head being disposed at a distance in the range of about 1 mm to 50 mm proximally from a proximal surface of the distal balloon.

In an embodiment, the method further comprises identifying impeded movement of the piston head, wherein cyclically modulating the level of pressure within the distal balloon comprises cyclically modulating the level of pressure within the distal balloon responsively to the identified impeded movement.

In an embodiment, the method comprises receiving a user-generated input indicative of impeded movement of the piston head, wherein cyclically modulating the level of pressure within the distal balloon comprises cyclically modulating the level of pressure responsively to the input.

In an embodiment, cyclically modulating the level of pressure within the distal balloon comprises cycling the level of pressure within the distal balloon irrespective of any indication of impeded movement of the piston head and/or substantially whenever the pressure seal between the piston head and the wall of the GI tract lumen is maintained during the distal advancement of the piston head.

In an embodiment, cyclically modulating the level of pressure within the distal balloon comprises modulating the level of pressure within the distal balloon such that a maximum diameter of the distal balloon during a plurality of cycles is 10 mm to 65 mm.

In an embodiment, cyclically modulating the level of pressure within the distal balloon comprises at least one of the followings: modulating the level of pressure within the distal balloon according to a cycle having a length of 0.5 seconds to 10 seconds, in particular a length of 2 seconds to 6 seconds; setting the level of pressure within the distal balloon to be at a minimum for at least 0.5 seconds in a plurality of cycles and at a maximum for at least 10 seconds in a plurality of cycles; setting a minimum pressure level of the distal balloon during a plurality of cycles to be less than 10 mbar, in particular less than 1 mbar, in particular substantially 0 mbar; setting a maximum pressure level of the distal balloon during a plurality of cycles to be greater than 20 mbar, in particular greater than 60 mbar.

In an embodiment, cyclically modulating the level of pressure within the distal balloon comprises actuating a suction source to suck fluid from the distal balloon.

In an embodiment, cyclically modulating the level of pressure within the distal balloon comprises passively allowing fluid to vent from the distal balloon.

DETAILED DESCRIPTION OF THE EMBODIMENTS

Figure 1A:
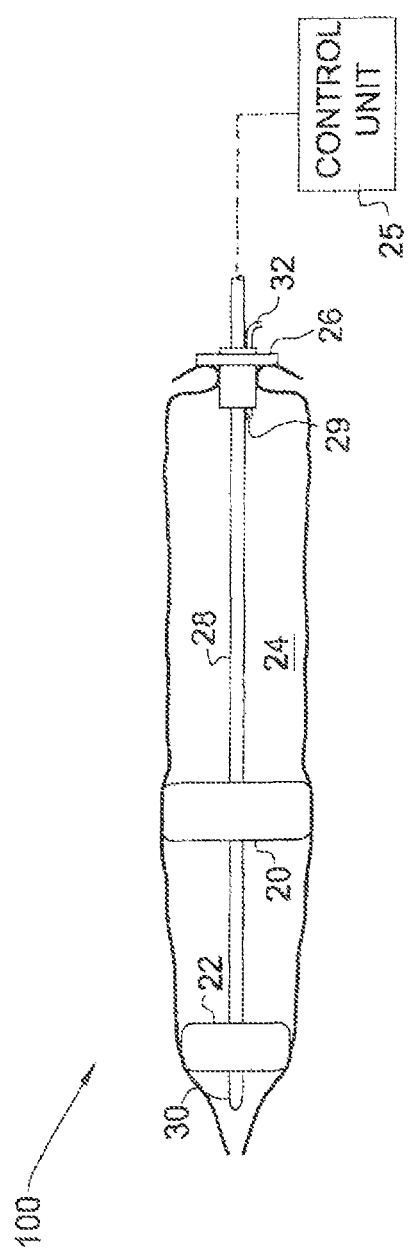
FIGS. 1A-1B are schematic illustrations of a piston head and a distal balloon disposed within a subject's GI tract, in accordance with an embodiment of the present invention.

Reference is now made to FIG. 1A, which is a schematic illustration of an example of an imaging apparatus 100 according to an embodiment of the present invention. The imaging apparatus 100 comprises a piston head 20 and a distal balloon 22 disposed within a subject's GI tract lumen 24 and a control unit 25, in accordance with an embodiment of the present invention. The piston head 20 is coupled to a distal portion of the carrier, and is configured to be inflated so as to form and maintain a pressure seal with a wall of the GI tract lumen, and be advanced distally through the GI tract in response to pressure from a fluid pressure source. The distal balloon 22 is coupled to the carrier, distally to the piston head and is configured and operable to be inflated so as to dilate the lumen thereby creating an imaging working space. The control unit 25 is configured and operable to control simultaneously the pressure level within the piston head and the pressure level within the distal balloon by maintaining a constant level of pressure within the piston head thereby maintaining the pressure seal between the piston head and the wall of the GI tract lumen and by cyclically modulating a level of pressure within the distal balloon facilitating the distal advancement of the piston head within the GI tract lumen.

An elongate carrier 28 is inserted into the lumen through a proximal opening of a gastrointestinal (GI) tract lumen. In the specific but non-limiting example of FIG. 1A, a guide member 26 is inserted into a proximal opening of a lumen of a subject's body, for example, a GI tract lumen 24, the elongated carrier 28 being inserted into the lumen through a bore in the guide member. An image-capturing device 30 configured to image the GI track lumen is typically mounted on carrier 28 distal to distal balloon 22.

It should be understood that the distal balloon is also configured and operable to create a space between the GI track and the image-capturing device to facilitate the imaging of the GI track.

Figure 1B:
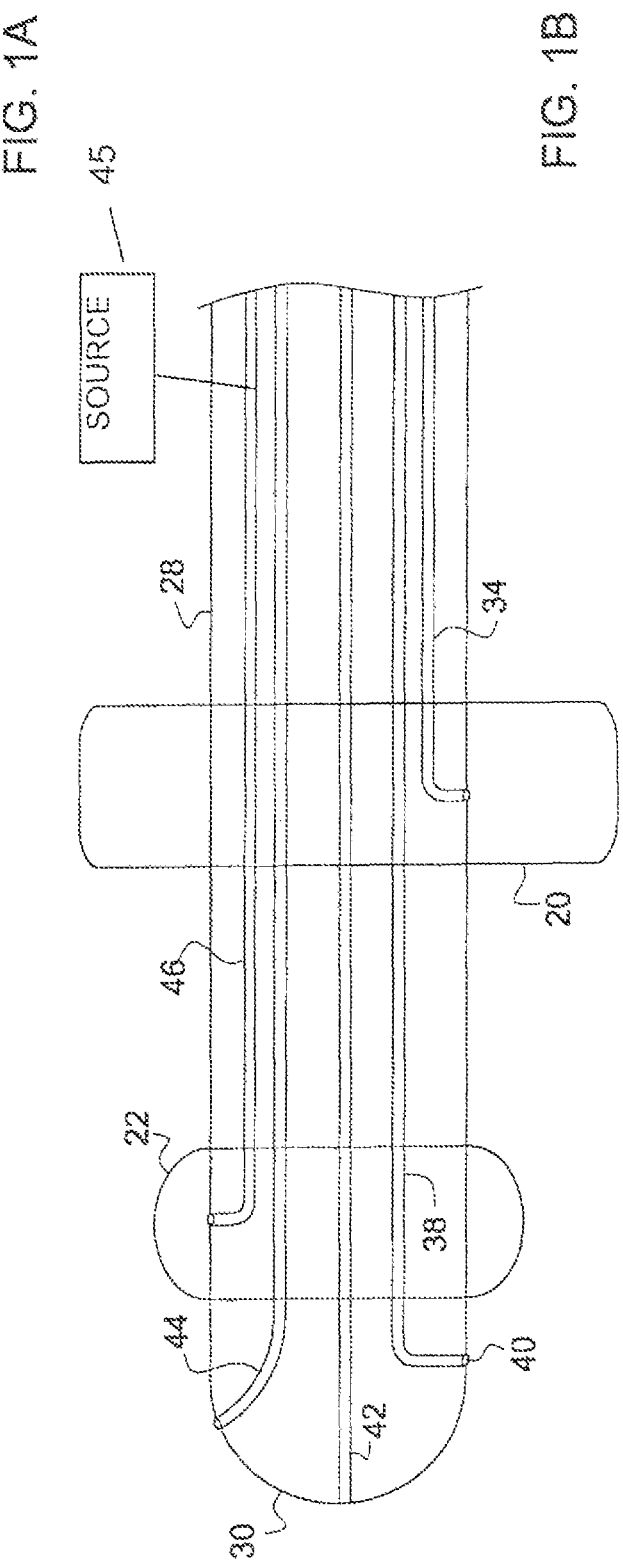

Reference is made to FIG. 1B illustrating an enlarged view of a portion of the imaging apparatus 100. Carrier 28 includes a piston head passageway 34 in fluid communication with piston head 20, connected to a source 32 of a pressurized biologically-compatible fluid, such as but not limited to, a source of pressurized air, $CO_2$ or water (not shown) for inflating piston head 20. In some embodiments, guide member 26 is formed with a source passageway 29 connected to the same source 32 or to another source.

For some applications, the piston head-inflation fluid pressure source is regulated to maintain a generally constant pressure within piston head 20, regardless of changes of volume of the piston head which occur in response to diameter changes of GI tract lumen 24. For example, the piston head is configured to have a diameter of 25 mm to 100 mm when the piston head is in its inflated state thereof.

A vent tube 38 may pass through or around piston head 20 (and through or around distal balloon 22), having an opening 40 distal to piston head 20 through which fluid is ventable to the outside. That is, the proximal end of vent tube 38 vents the fluid past guide member 26 to the outside.

A power supply tube 42 (e.g., containing electrical wires, fiber optics, etc.) may pass through carrier 28, for connection to image-capturing device 30.

In some embodiments, a fluid supply tube 44 passes through carrier 28 and is connected to a fluid source (not shown), e.g., pressurized water, for cleaning the area near image-capturing device 30, or, in combination with vent tube 38, for cleaning GI tract lumen 24 itself.

The piston head 20 is advanced through the GI tract by applying pressure to the piston head, by passing fluid (e.g., air) into the portion of the GI tract that is proximal to the piston head, via passageway 34. During advancement of the piston head, vent tube 38 vents to the outside the pressure that accumulates due to the advancement of the piston head. The piston head is typically withdrawn proximally through the GI tract by creating a pressure difference in a reverse manner, to actively propel piston head 20 together with carrier 28 proximally. Pressurized fluid (e.g., air) from another (e.g. third) fluid pressure source (not shown) is introduced to the distal side of piston head 20, via a pressure-application tube passing through or around piston head 20. The distal balloon is therefore controlled independently from the piston head via a different fluid pressure source 45.

Optionally, vent tube 38 serves as the pressure-application tube during withdrawal. The pressurized fluid creates greater fluid pressure acting on the distal side of piston head 20 than on the proximal side of piston head 20, thereby proximally propelling the piston head and the carrier. During the advancement and/or the withdrawal of the piston head through the GI tract, imaging device 30 images the GI tract.

In some embodiments, a further passageway 46 passes through or around piston head 20. The apparatus 100 may have a further, fluid pressure source 45 in fluid communication with the further passageway 46 and the distal balloon 22. A control unit 25 controls simultaneously and independently a flow of fluid from the further fluid pressure source 45 into distal balloon 22, via passageway 46. Fluid is removed from distal balloon 22 past guide member 26 to the outside, via passageway 46.

In some embodiments, a first passageway supplies fluid to the distal balloon and a second passageway removes fluid from the distal balloon. Typically, the fluid pressure source supplies a pressurized biologically-compatible fluid, such as but not limited to, pressurized air, $CO^2$ or water. For some applications, fluid is vented from the distal balloon via passageway 46 in a passive manner (i.e. by permitting the passage of the fluid out of the lumen). Alternatively, passageway 46 is coupled to a suction source, and the suction source actively sucks fluid from the distal balloon. For example, control unit 25 controls the suction source.

Figure 2A:
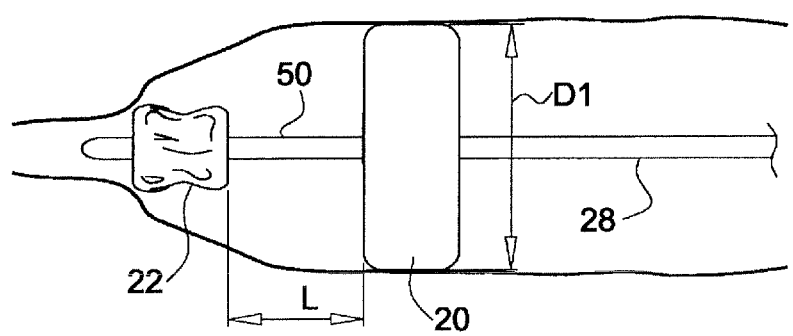
FIGS. 2A-2B are schematic illustrations of the distal balloon respectively in deflated and inflated states thereof, in accordance with an embodiment of the present invention.
Figure 2B:
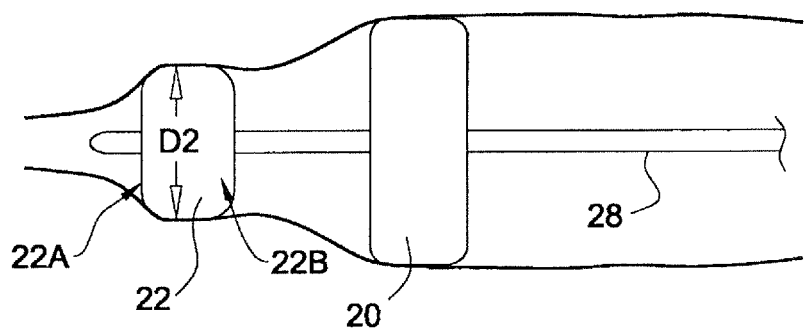

Reference is now made to FIGS. 2A-2B, which are schematic illustrations of distal balloon 22 respectively in deflated (2A) and inflated states (2B) thereof, in accordance with an embodiment of the present invention. In some embodiments, piston head 20 is inflated so as to form and maintain a pressure seal with a wall of GI tract lumen 24 (as shown, for example, in FIG. 1A). The piston head is advanced distally through the GI tract in response to pressure from a fluid pressure source, as described hereinabove.

Control unit 25 (shown in FIG. 1A) cycles the pressure level within the distal balloon while maintaining the pressure seal between the piston head and the wall.

In some embodiments, the control unit cycles the level of pressure within the distal balloon when distal movement of the piston head is impeded. The control unit 25 identifies movement of piston head 20 (for example, by using an acceleration sensor coupled to the piston head), and cycles the level of pressure within distal balloon 22 responsively to a parameter of the identified movement. Alternatively or additionally, the control unit receives a user-generated input indicative of impeded movement of the piston head, and cycles the level of pressure within the distal balloon responsively to the input. For some applications, the control unit cycles the level of pressure within the distal balloon irrespective of any indication of impeded movement of the piston head. For example, the control unit may continuously cycle the level of pressure within the distal balloon substantially whenever the pressure seal between the piston head and the wall of the GI tract lumen is maintained during the distal advancement of the piston head.

For some applications, a maximum diameter D2 of distal balloon 20 is 10 mm to 65 mm, while control unit 25 cycles the level of pressure within the distal balloon. Distal balloon 22 is typically coupled to piston head 20 by a tube 50 which may be a separate or integral portion of carrier 28. In some embodiments, tube 50 has a hardness of 30-38 shore A. Typically, length L of tube 50 is 5 mm to 30 mm in embodiments in which the maximum diameter D2 of the balloon is 10 mm to 50 mm, and is 20 mm to 50 mm in embodiments in which the maximum diameter D2 of the balloon is 50 mm to 65 mm.

In some embodiments, the control unit is configured to cycle the level of pressure within the distal balloon to selectively collapse or expand a distal and/or proximal ends (22A and 22B) of the balloon.

Figure 3A:
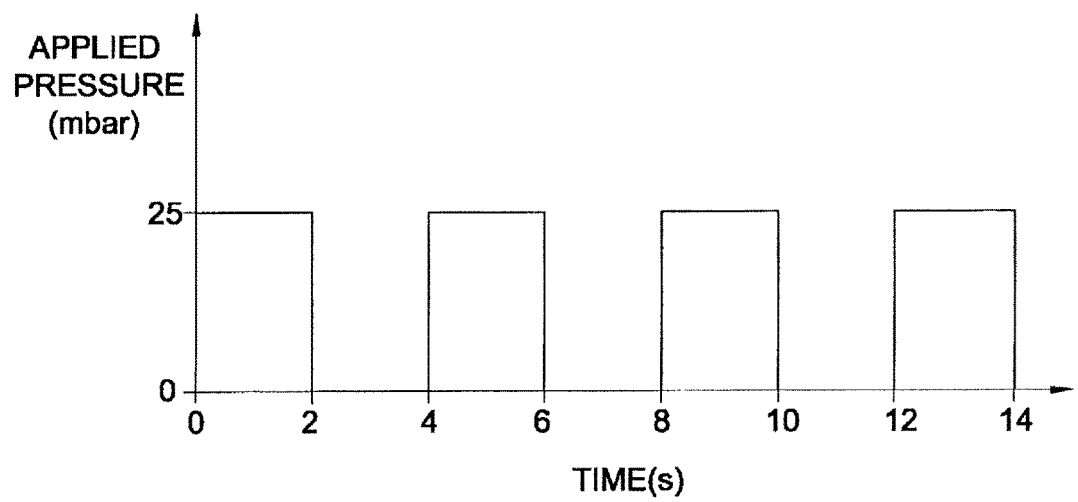
FIGS. 3A-3B are graphs illustrating cyclical modulation of the pressure within the distal balloon, in accordance with an embodiment of the present invention.
Figure 3B:
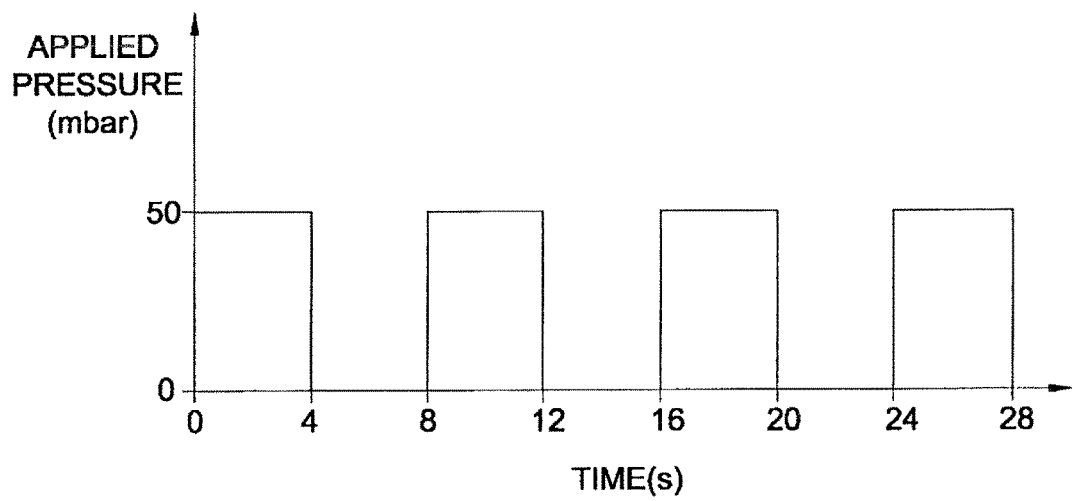

Reference is now made to FIGS. 3A-3B, which is a graph illustrating cyclical modulation of the pressure within distal balloon 22, in accordance with an embodiment of the present invention. The graph 3A shows a 4 second cycle, according to which the balloon pressure is at a minimum pressure of zero mbar for 2 seconds of each cycle, and at a maximum of 25 mbar for 2 seconds of each cycle. The graph 3B shows an 8 second cycle, according to which the balloon pressure is at a minimum pressure of zero mbar for 4 seconds of each cycle, and at a maximum of 50 mbar for 4 seconds of each cycle.

Typically, cyclic modulation of the pressure within distal balloon 22 facilitates the advancement and/or withdrawal of piston head 20, if advancement and/or withdrawal had been impeded by interactions between the apparatus and the GI tract lumen.

It should be understood that the apparatus has the ability of to be withdrawn proximally through the body lumen in response to pressure from the fluid pressure source by applying fluid pressure to an external surface of the piston head creating a pressure difference. Pressurized fluid (e.g., air) from a fluid pressure source is introduced to the distal side of piston head 20, via a pressure-application tube passing through or around piston head 20. Optionally, vent tube 38 serves as the pressure-application tube during withdrawal. The pressurized fluid creates greater fluid pressure acting on the distal side of piston head 20 than on the proximal side of piston head 20, thereby proximally propelling the piston head and the carrier. A vent tube between the proximal side of piston head 20 and outside the lumen may assist in creating the pressure difference across piston head 20, either passively or actively via applied suction. During the withdraw of the piston head, the pressure level within the distal balloon is not cyclically modulated, but maintained at a constant minimum pressure, inflating the distal balloon to create a space between the GI track and the image-capturing device mounted on the carrier distally to the distal balloon to facilitate the imaging of the GI track as described above. The distal balloon being inflated enables to flood the image capturing device within the body lumen.

In some embodiments, the apparatus 100 includes a suction source (not shown) configured to actively sucks fluid from the distal balloon. The control unit 25 is configured to cycle the level of pressure within the distal balloon by controlling the suction source The cycle of the level of pressure of the suction source has a length in the range of about 0.5 seconds to 5 seconds.

Alternatively or additionally, the fluid is vented from the distal balloon passively. The cycle of the level of pressure within the distal balloon has a length, in the range of about 1.5 seconds to 10 seconds. In some embodiments, the cycle is such that the distal balloon pressure level is at a minimum for about 0.5-4 seconds in a plurality of cycles and at a maximum for at least 0.5-4 seconds in a plurality of cycles.

In some embodiments, the minimum pressure within the distal balloon during a plurality of cycles is less than 10 mbar, for example, less than 1 mbar, e.g., substantially zero mbar. In some embodiments, the maximum pressure within the distal balloon during a plurality of cycles is greater then 20 mbar, e.g., greater than 65 mbar.

For example, the distal balloon is pulsed with a target pressure of about 50-60 mbar. Several modes of operation are possible: (1) a constant pressure is applied during a cycle in the range of about 0 to 6 seconds (preferably 2 seconds). An active deflation is then performed and no pressure is applied for about 0-2 seconds. (2) A constant pressure is applied for 0 to 6 seconds (typically 2) with a closed channel (in this case, the balloon is not controlled or cannot reduce its volume even if surrounding pressure rises). An active deflation is then performed and no pressure is applied for about 0-2 seconds. (3) The distal balloon may be deflated and inflate again immediately (fastest frequency).

It should be understood that as described above, the lower part of the GI track linking up with the rectum is a thin portion in which the insertion of the piston head and its inflation is a difficult task. To solve the above-mentioned problem, the distal balloon having a diameter substantially smaller than the piston head, and being inserted before the piston head in the lumen, may be inflated to form a pressure seal with the GI track by maintaining a constant level of pressure to enable the distal advancement of the apparatus.

In some embodiments, the distal balloon is used to drive the piston head and the entire apparatus distally. The piston head is then inflated with a pressure which is lower than the supplied rear pressure (i.e. the pressure acting on the proximal side of the piston head). In this mode, the piston head is normally collapsed due to the lower pressure than its surrounding, but once a leakage is observed (for example when the distal balloon does not create a pressure seal with the colon wall), the rear pressure is rapidly reduced (due to the leakage), causing the piston head to create a pressure seal with the colon. Therefore, the capability of the system of the present invention to control the piston head and the distal balloon separately enables this type of operation needed in particularly when a leakage exists between the piston head and the wall of the colon and when the pressure at the proximal side of the piston head drops. By using this mode of operation, the piston head increase its volume due to the surrounding pressure drop, enabling a better seal with the colon wall and the prevention of further leakage.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising: forming a pressure seal between a piston head and a wall of a gastrointestinal (GI) tract lumen, the piston head being disposed proximally to a distal balloon; while the pressure seal between the piston head and the wall of the GI tract lumen is maintained, applying fluid pressure to an external surface of the piston head to thereby advance the piston head and the distal balloon distally through the lumen; and continuously cyclically modulating a level of pressure within the distal balloon, while maintaining the pressure seal between the piston head and the wall of the GI tract lumen to dilate the lumen thereby creating an imaging working space through which advancement of the piston head is facilitated.

2. The method according to claim 1, comprising identifying impeded movement of the piston head, wherein cyclically modulating the level of pressure within the distal balloon comprises cyclically modulating the level of pressure within the distal balloon responsively to the identified impeded movement.

3. The method according to claim 1, comprising receiving a user generated input indicative of impeded movement of the piston head, wherein cyclically modulating the level of pressure within the distal balloon comprises cyclically modulating the level of pressure responsively to the input.

4. The method according to claim 1, wherein cyclically modulating the level of pressure within the distal balloon comprises actuating a suction source to suck fluid from the distal balloon.

5. The method according to claim 1, wherein cyclically modulating the level of pressure within the distal balloon comprises passively allowing fluid to vent from the distal balloon.

* * * * *